(12) United States Patent
Robinson

(10) Patent No.: US 9,364,262 B2
(45) Date of Patent: Jun. 14, 2016

(54) BONE SCREW COUPLING ASSEMBLY

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 242 days.

(21) Appl. No.: 13/935,680

(22) Filed: Jul. 5, 2013

(65) Prior Publication Data

US 2014/0005724 A1 Jan. 2, 2014

Related U.S. Application Data

(63) Continuation of application No. 13/540,049, filed on Jul. 2, 2012, now Pat. No. 8,491,640.

(51) Int. Cl.
*A61B 17/70* (2006.01)

(52) U.S. Cl.
CPC ......... *A61B 17/7002* (2013.01); *A61B 17/7035* (2013.01)

(58) Field of Classification Search
CPC ........... A61B 17/7032; A61B 17/7035; A61B 17/7037; A61B 17/7038; A61B 17/7047
See application file for complete search history.

(56) References Cited

U.S. PATENT DOCUMENTS

| | | | |
|---|---|---|---|
| 2,855,232 A * | 10/1958 | Kozak | 403/132 |
| 4,946,458 A * | 8/1990 | Harms et al. | 606/305 |
| 5,010,879 A * | 4/1991 | Moriya et al. | 606/276 |
| 5,281,222 A * | 1/1994 | Allard et al. | 606/54 |
| 5,312,405 A * | 5/1994 | Korotko et al. | 606/278 |
| 5,380,326 A * | 1/1995 | Lin | 606/330 |
| 5,630,817 A * | 5/1997 | Rokegem et al. | 606/269 |
| 6,210,413 B1 | 4/2001 | Justis et al. | |
| 6,254,602 B1 | 7/2001 | Justis | |
| RE37,665 E | 4/2002 | Ralph et al. | |
| 6,413,257 B1 * | 7/2002 | Lin et al. | 606/264 |
| 6,911,030 B1 | 6/2005 | Vanacker et al. | |
| 7,776,067 B2 * | 8/2010 | Jackson | 606/246 |
| 7,850,718 B2 * | 12/2010 | Bette et al. | 606/267 |
| 7,875,065 B2 | 1/2011 | Jackson | |
| 7,892,259 B2 | 2/2011 | Biedermann et al. | |
| 7,901,436 B2 * | 3/2011 | Baccelli | 606/272 |
| 8,100,948 B2 * | 1/2012 | Ensign et al. | 606/267 |
| 8,221,472 B2 | 7/2012 | Peterson et al. | |
| 8,257,398 B2 | 9/2012 | Jackson | |
| 8,267,969 B2 | 9/2012 | Altarac et al. | |
| 8,491,640 B1 * | 7/2013 | Robinson | 606/267 |
| 2003/0125741 A1 | 7/2003 | Biedermann et al. | |
| 2004/0097933 A1 | 5/2004 | Lourdel et al. | |
| 2005/0027292 A1 * | 2/2005 | Bernard et al. | 606/61 |
| 2005/0228385 A1 | 10/2005 | Iott et al. | |
| 2006/0229615 A1 | 10/2006 | Abdou | |
| 2007/0093817 A1 * | 4/2007 | Barrus et al. | 606/61 |
| 2008/0243193 A1 | 10/2008 | Ensign et al. | |
| 2009/0248088 A1 * | 10/2009 | Biedermann | 606/305 |
| 2011/0040336 A1 | 2/2011 | Hammill, Sr. et al. | |
| 2012/0029569 A1 | 2/2012 | Iott et al. | |
| 2012/0172932 A1 | 7/2012 | Biedermann et al. | |
| 2012/0265257 A1 | 10/2012 | Jackson | |

* cited by examiner

*Primary Examiner* — Mary Hoffman

(74) *Attorney, Agent, or Firm* — FisherBroyles, LLP; Anthony J. DoVale

(57) ABSTRACT

A coupling assembly is presented. The coupling assembly is used to selectively couple a bone screw having an elongate shaft and a head to an elongate rod. The coupling assembly has a coupling element configured to engage the head of a bone screw, as well as the elongate rod. When the elongate rod is engaged by the portion of the top of the coupling element, the coupling element does not extend above a top most portion of elongate rod.

22 Claims, 12 Drawing Sheets

BONE SCREW COUPLING ASSEMBLY

CONTINUITY

This application is a continuation of and claims priority to and the benefit of U.S. patent application Ser. No. 13/540,049, now issued U.S. Pat. No. 8,491,640 entitled "Bone Screw Coupling Assembly," filed on Jul. 2, 2012 and which is incorporated herein in its entirety.

FIELD OF THE INVENTION

Presented herein is a coupling assembly. More specifically, a coupling assembly for use with a bone screw used in spinal surgery is presented.

BACKGROUND OF THE INVENTION

Spinal surgeons often treat spinal disorders with spinal fusion augmented with elongated spinal rods connected to the spine with pedicle screws. Such "rod assemblies" generally comprise one or two spinal rods and a plurality of screws inserted through the pedicles and into their respective vertebral bodies. The screws are provided with connectors, for coupling the spinal rods to the screws. The spinal rods extend along the longitudinal axis of the spine, coupling to the plurality of screws via their connectors. The aligning influence of the rods forces the patient's spine to conform to a more appropriate shape.

SUMMARY

Presented herein is a coupling assembly used to selectively couple a bone screw having an elongate shaft and a head to an elongate rod. The elongate rod is, for example, used to connect a plurality of screws together. The coupling assembly has a coupling element configured to engage the head of a bone screw, as well as the elongate rod. The assembly has an outer housing configured to work with the coupling assembly to secure the coupling assembly to the head of the bone screw and to the elongate rod.

In an exemplified aspect, when the elongate rod is engaged by the portion of the top of the coupling element, the coupling element does not extend above a top most portion of elongate rod. The resulting lower profile of the coupling element provides a coupling assembly that does not protrude as far from the vertebrae as in conventional systems. Another benefit of the coupling assembly described herein is that, since the outer housing biases the coupling element by moving in the direction transverse to the central axis of the coupling assembly, the coupling element can seat in close proximity to the portion of the vertebrae in which the bone screw is affixed, minimizing the space between the vertebrae and the bottom of the coupling element.

Other aspects and embodiments of the coupling assembly are described herein. This description is meant to fully describe the coupling assembly, but not limit its design, function, or application.

BRIEF DESCRIPTION OF THE DRAWINGS

These and other features of the preferred embodiments of the present invention will become more apparent in the detailed description in which reference is made to the appended drawings wherein.

DETAILED DESCRIPTION OF THE INVENTION

Figure 1:
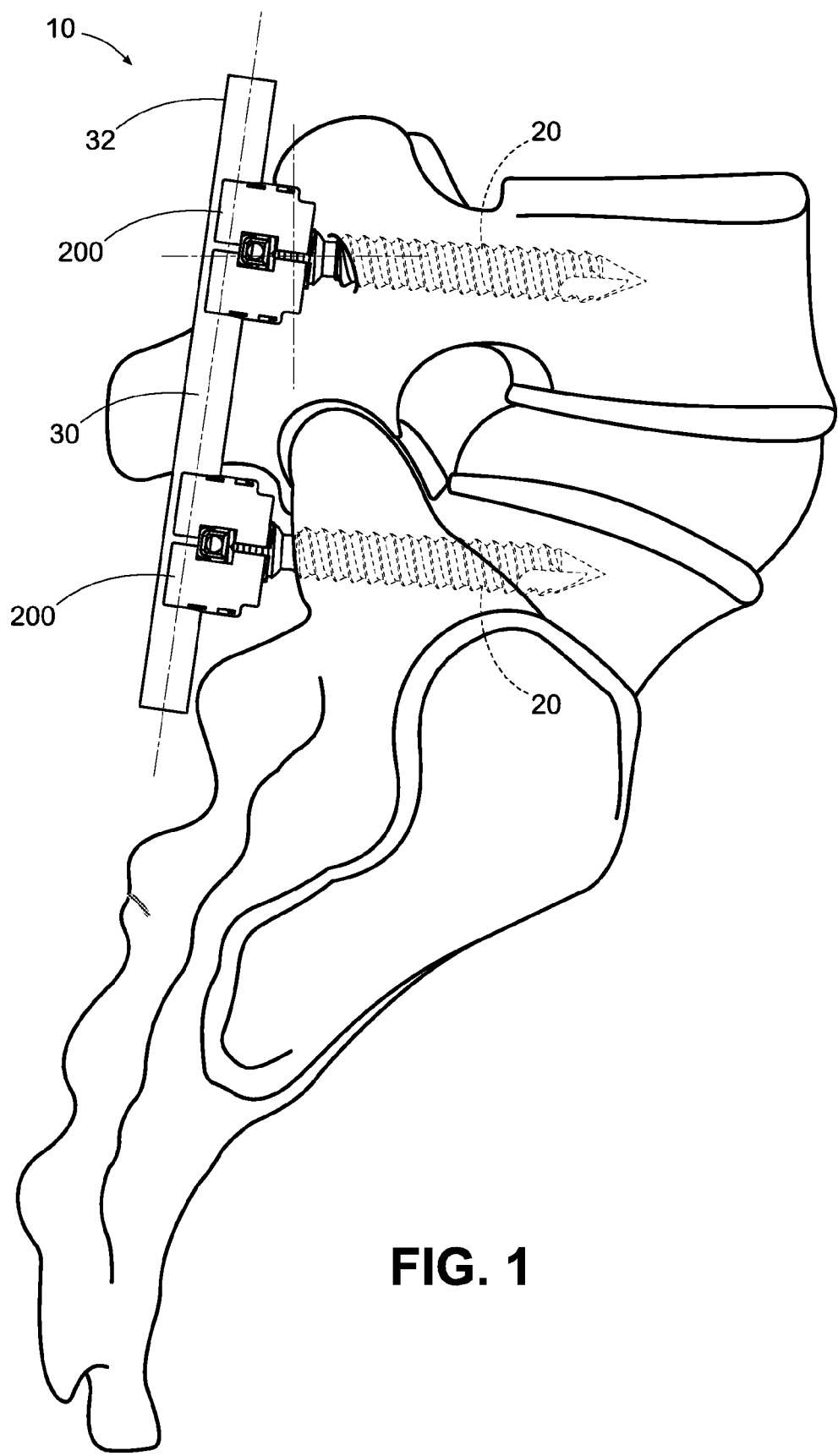
FIG. 1 is a side elevational view of one aspect of a coupling assembly as used with a bone screw system shown positioned in a human spine.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein is a coupling assembly 10 used to selectively couple a bone screw 20 having an elongate shaft 22 and a head 24 to an elongate rod 30. The elongate rod 30 is, for example, used to connect a plurality of screws together. The coupling assembly 10 has a coupling element 100 configured to engage the head 24 of a bone screw 20 and the elongate rod. The assembly has an outer housing 200 configured to work with the coupling assembly 10 to secure the coupling assembly 10 to the head 24 of the bone screw 20 and to the elongate rod 30.

In one aspect, a portion of the bottom 110 of the coupling element 100 is configured to engage the head 24 of the bone screw. In another aspect, a portion of the top 130 of the coupling element is configured to engage a portion of the elongate rod. The outer housing, in this aspect, is configured to selectively bias portions of the coupling element into engagement with the portion of the elongate rod 30 by moving portions of the outer housing toward the central axis Ac of the coupling assembly.

In an exemplified aspect, when the elongate rod is engaged by the portion of the top 130 of the coupling element 100, the coupling element does not extend above a top most portion 32 of elongate rod 30.

In yet another aspect, a portion of the top 130 of the coupling element 100 defines a saddle 140 with a first side 142 having an exterior surface 144 and a second side 146 having an exterior surface 148. In this aspect, the saddle 140 defines a rod receiving channel 150, wherein at least one of the exterior surfaces of the first or second sides of the saddle is angled with respect to the longitudinal axis AL of the rod receiving channel 150. In one exemplified aspect, the outer housing 200 has a first slider 210 comprising a body 212 and first and second spaced legs 214, 216. The body is configured to slide longitudinally, toward the central axis Ac, from a first position where the saddle is substantially open, thereby permitting ingress or egress of the elongate rod 30 with respect to the rod receiving channel 150, to a second position where at least one of the legs frictionally engages the angled exterior surface, biasing the respective side of the saddle toward the longitudinal axis to engage the elongate rod, thereby substantially retaining the elongate rod 30 therein the rod receiving channel.

Figure 2:
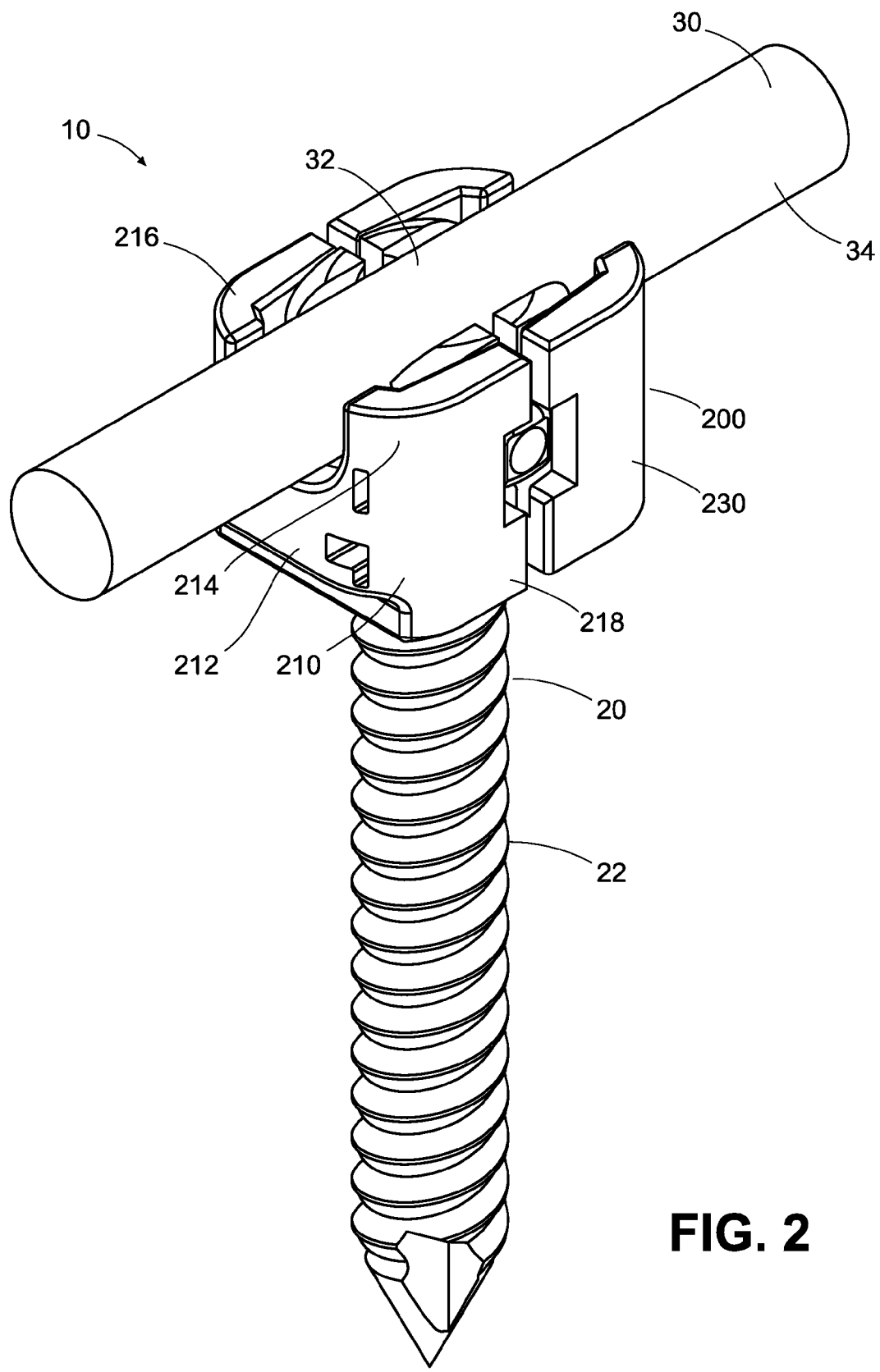
FIG. 2 is a perspective view of one aspect of a coupling assembly having an outer housing with two sliders in engagement with an elongate rod.

As illustrated in FIG. 2, the outer housing 200 can further comprise a second slider 230, oppositely disposed from the first slider 210. In this aspect, the first slider is configured to slide toward a midline portion 160 of the coupling element 100 from a first direction 162, and the second slider is configured to slide to the midline portion of the coupling element from a second direction 164.

The saddle 140 can be shaped to substantially conform to an exterior portion 34 of the elongate rod, thereby providing more surface area for the engagement between the saddle and the elongate rod.

In still another aspect, a portion of the bottom 110 of the coupling element defines a cradle 112 with a first side 114 and a second side 116. The cradle 112 defines a cavity 118 configured for receipt of the head 24 of the bone screw 20. In this aspect, at least one of the exterior surfaces 120, 122 of the first or second sides of the cradle is angled with respect to the longitudinal axis AL. Here, the first slider 210 comprises third and fourth spaced legs 218, 220, such that, when the body 212 is in the first position, the cradle is substantially open, thereby permitting movement of the head of the bone screw within the cavity 118. When the body is moved into the second position, at least one of the third or fourth legs frictionally engages the angled exterior surface of the respective side of the cradle 112, biasing the respective side of the cradle toward the longitudinal axis, at least partially closing the cradle, thereby substantially fixing the orientation of the head 24 of the bone screw with respect to the coupling element 100. The third and fourth spaced legs can be substantially separate or integral with the first and second spaced legs. It is also contemplated that the third and fourth spaced legs can actuate together with the first and second spaced legs or separate therefrom.

The exterior surfaces 144, 148 of the at least one of the first and second sides 142, 146 of the saddle 140 are angled with respect to the longitudinal axis of the rod receiving channel. Of course, it is also contemplated that both of the exterior surfaces of the first and second sides of the saddle are angled with respect to the longitudinal axis. In one aspect, the exterior surface of the first side angles away from the longitudinal axis toward the midline, and the exterior surface of the second side also angles away from the longitudinal axis toward the midline.

In one exemplified aspect, the portion of the at least one leg of the slider that frictionally engages the angled exterior surface is an interior portion that is angled to compliment the exterior surface of the respective side in which it frictionally engages.

As one can appreciate, an outer housing 200 with one slider has been presented, as has an outer housing with two sliders. In the aspect with two sliders, the sliders can actuate toward one another and can be mirror images of each other, where the second slider would also comprise first and second legs, as well as third and fourth legs, when necessary.

Since the outer housing is used to bias the coupling element into engagement with the head 24 of the bone screw, as well as the elongate rod, in one aspect, the coupling element comprises a substantially deformable material. The substantially deformable material can comprise Titanium or a Titanium alloy, such as Ti 6-4 ELI. As such, the outer housing comprises a material with a hardness greater than the substantially deformable material. For example, and not meant to be limiting, the outer housing can comprise Cobalt Chromium.

In one aspect, at least one of the first and second sides of the saddle, or both, optionally defines a longitudinal slot 170 configured to permit the saddle to deform inwardly toward the longitudinal axis. The longitudinal slot provides a weak point enabling the saddle to deform more easily. In another aspect, each side of the saddle can be bisected, further weakening the saddle and making it easier for the outer housing to bias it.

Figure 3:
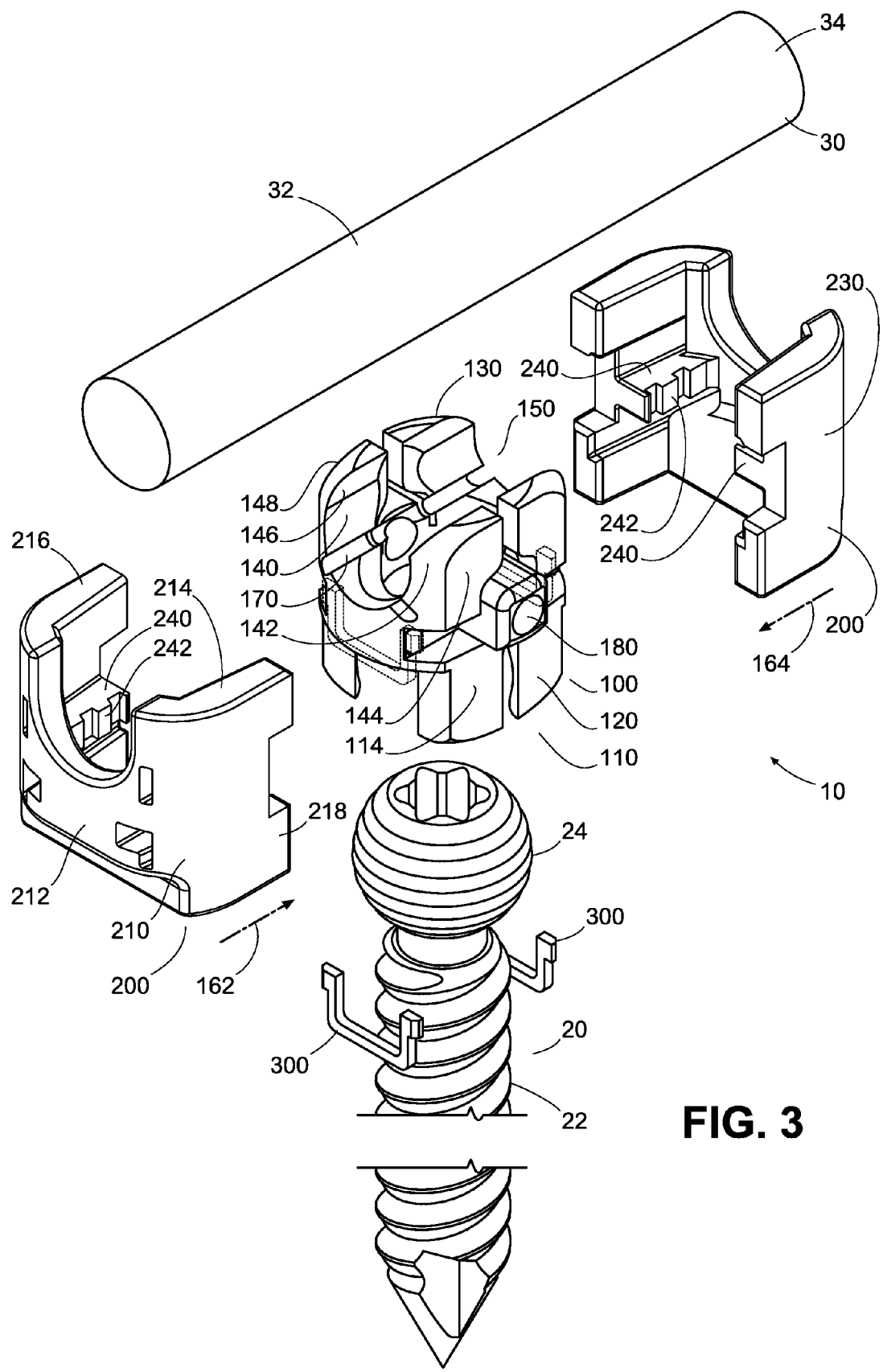
FIG. 3 is an exploded view of the coupling assembly of FIG. 2, showing a bone screw for acceptance into a portion of the bottom of the coupling element.
Figure 4:
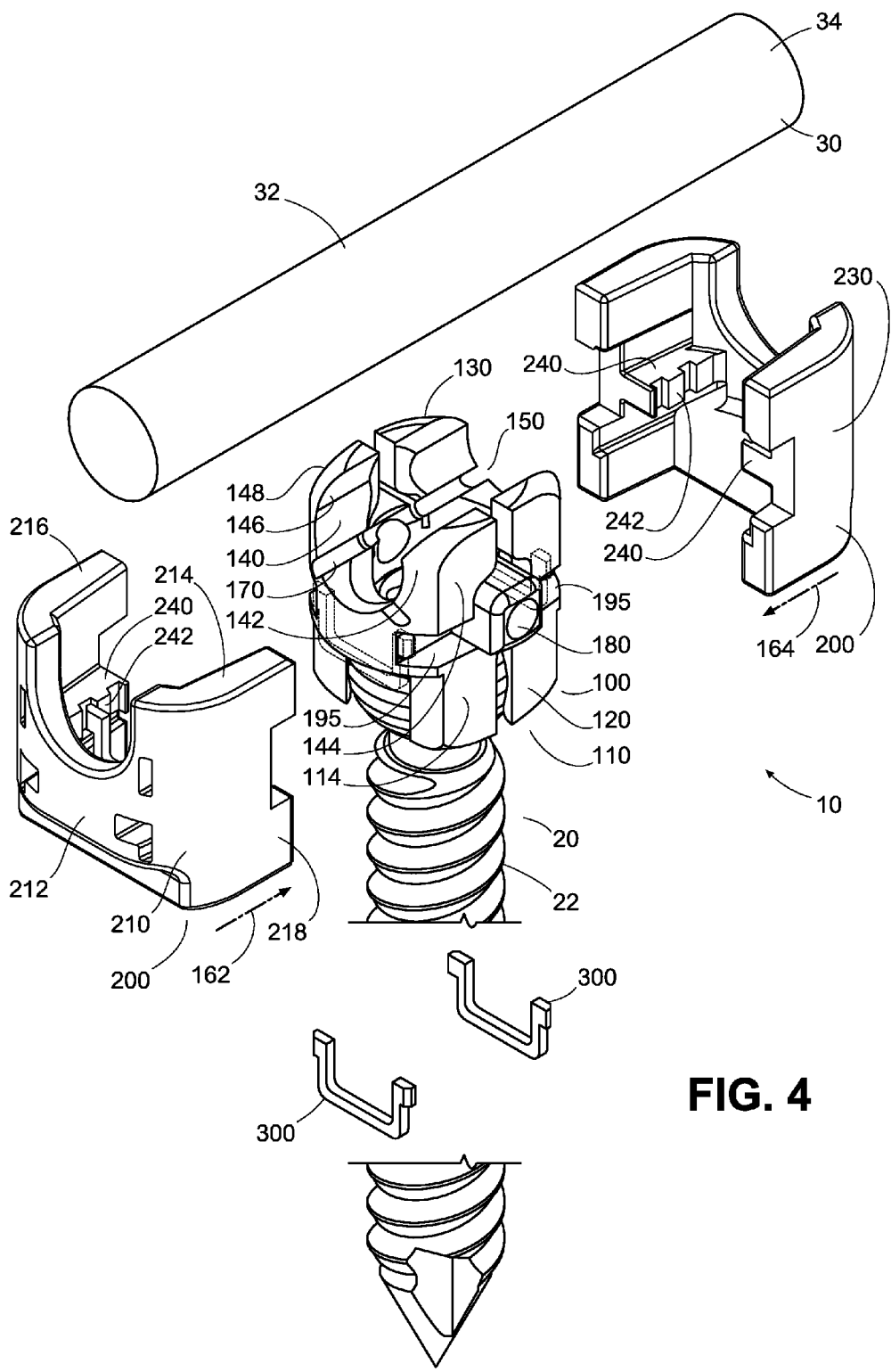
FIG. 4 is an exploded view of the coupling assembly of FIG. 2, showing the head of a bone screw positioned therein a cavity formed by the cradle of a coupling element.
Figure 5:
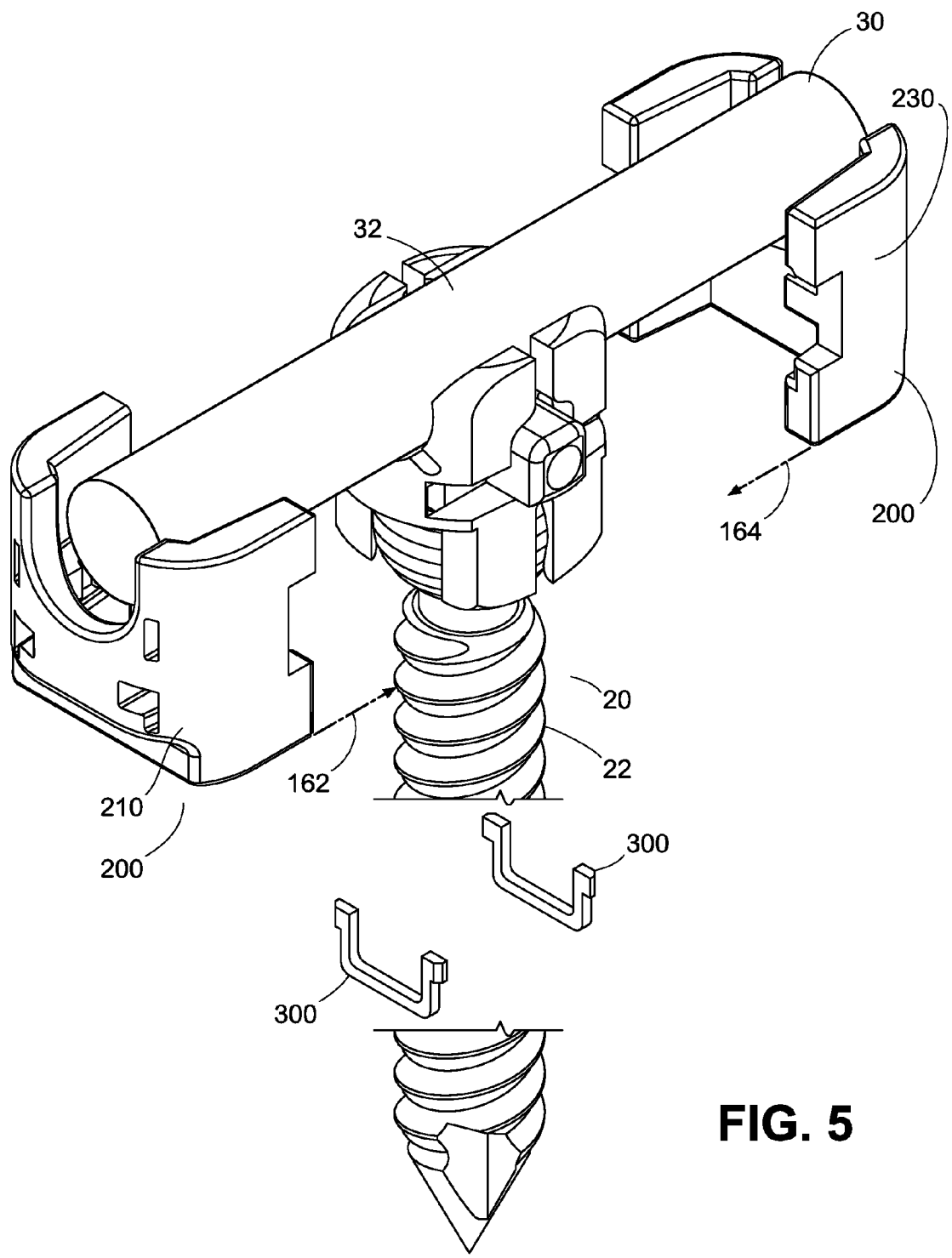
FIG. 5 is an exploded view of the coupling assembly of FIG. 2, showing an elongate rod positioned therein the rod receiving channel formed by the saddle of the coupling element.
Figure 6:
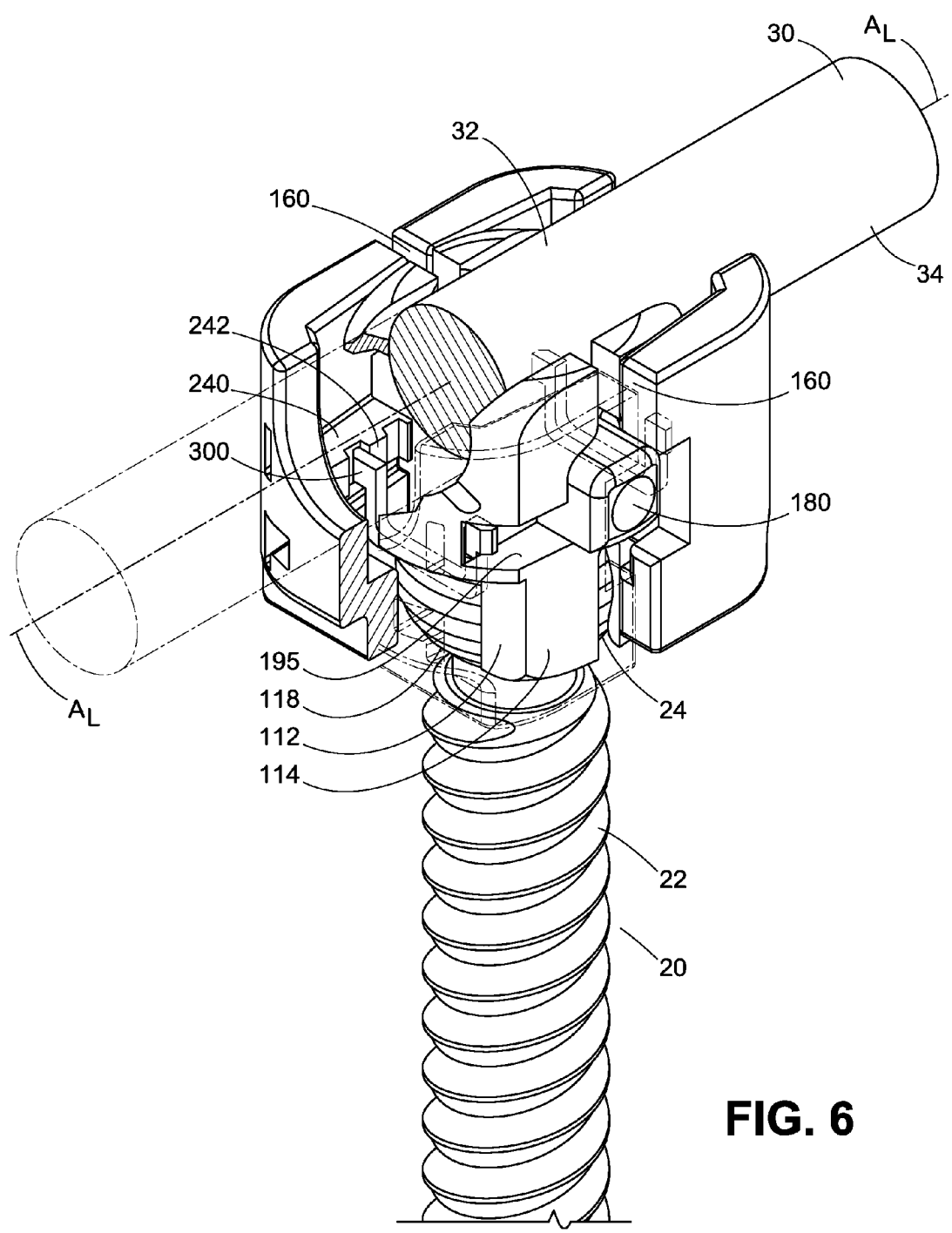
FIG. 6 is a partially transparent perspective view of the coupling assembly of FIG. 2, illustrating the interlocking of the bias element with the ribbed portion of the longitudinal beam.
Figure 7:
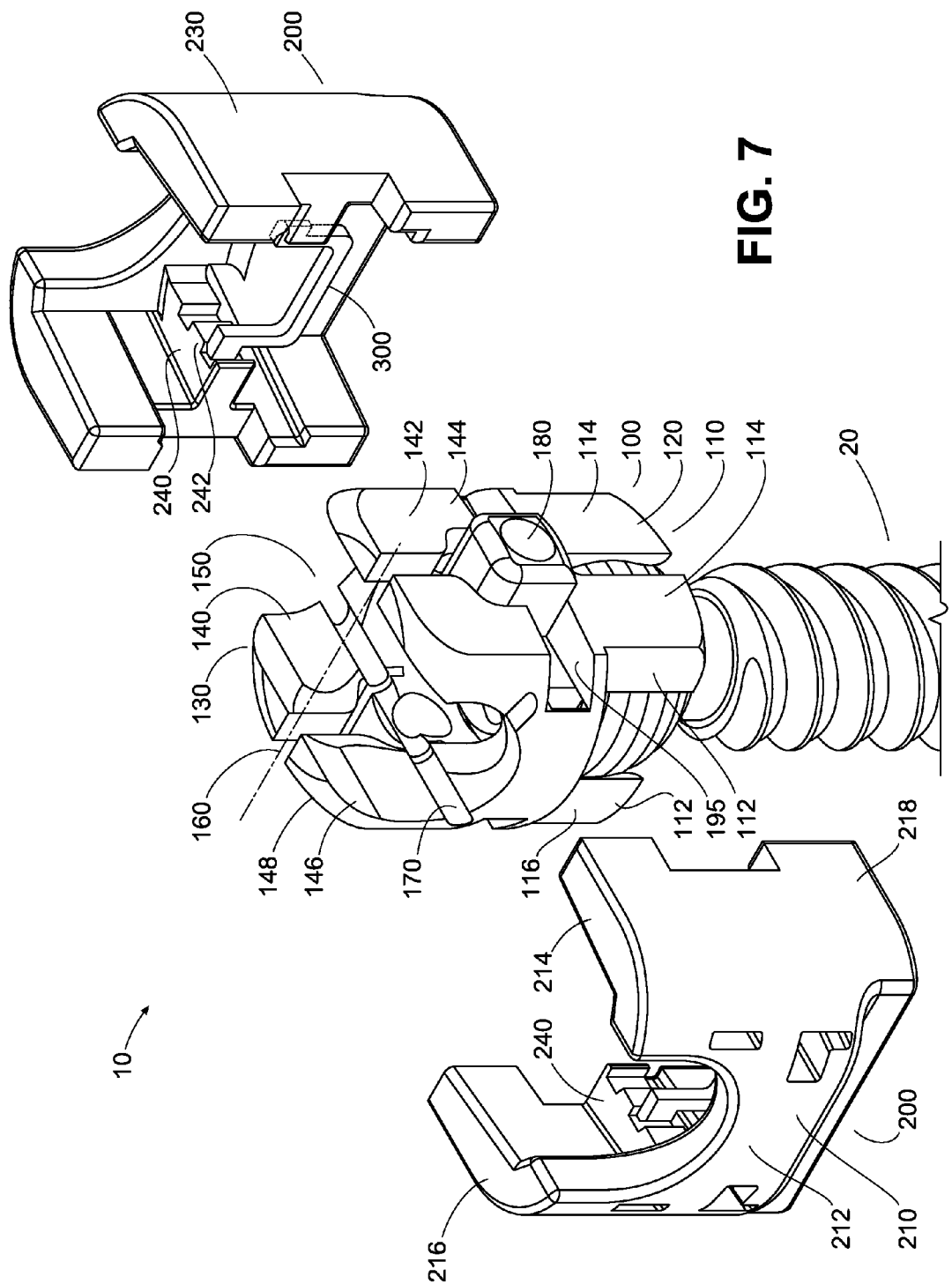
FIG. 7 is an exploded perspective view of the coupling assembly of FIG. 2, showing two sliders.
Figure 8:
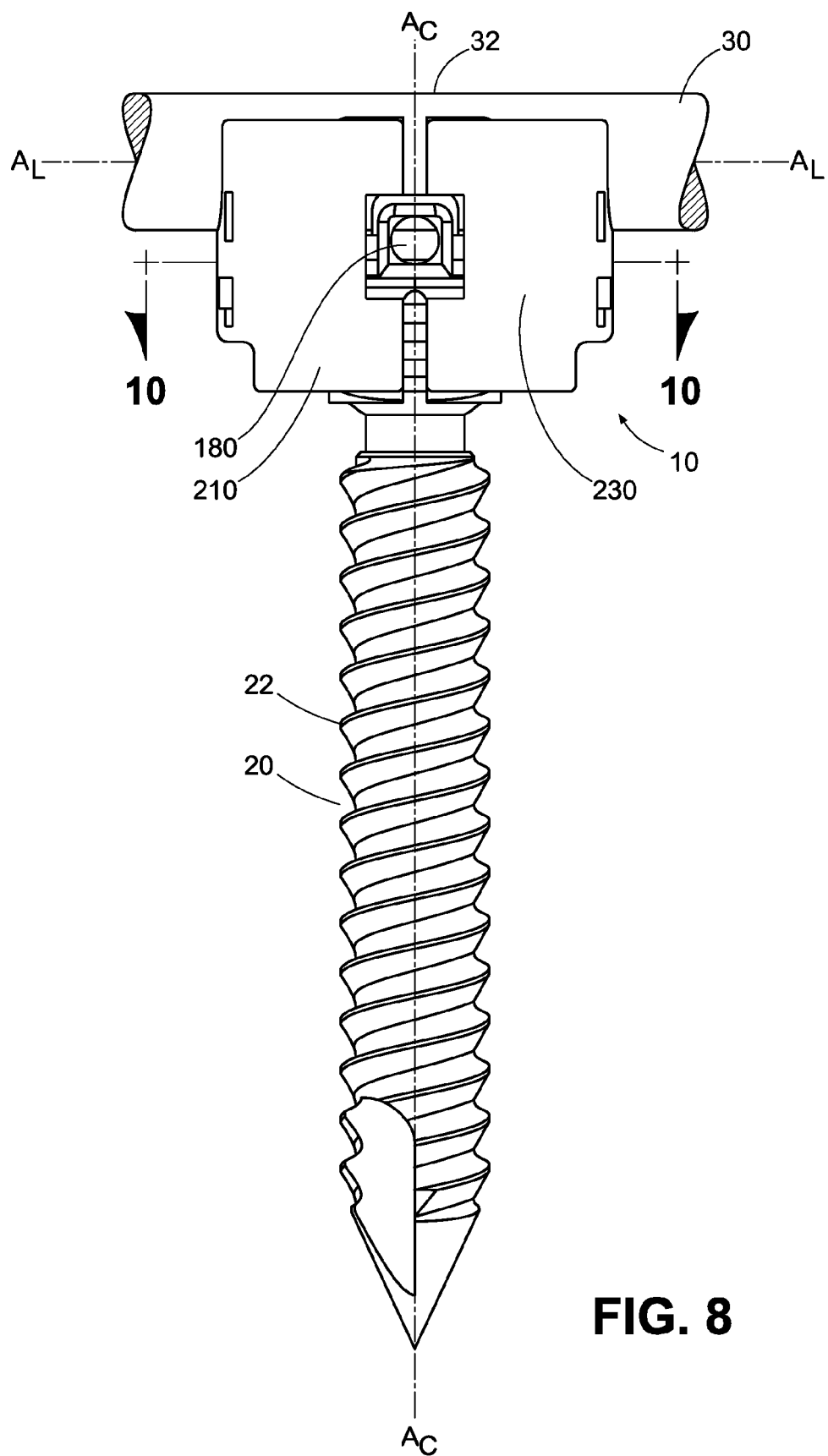
FIG. 8 is a side elevational view of the coupling assembly of FIG. 2 in the closed position.
Figure 9:
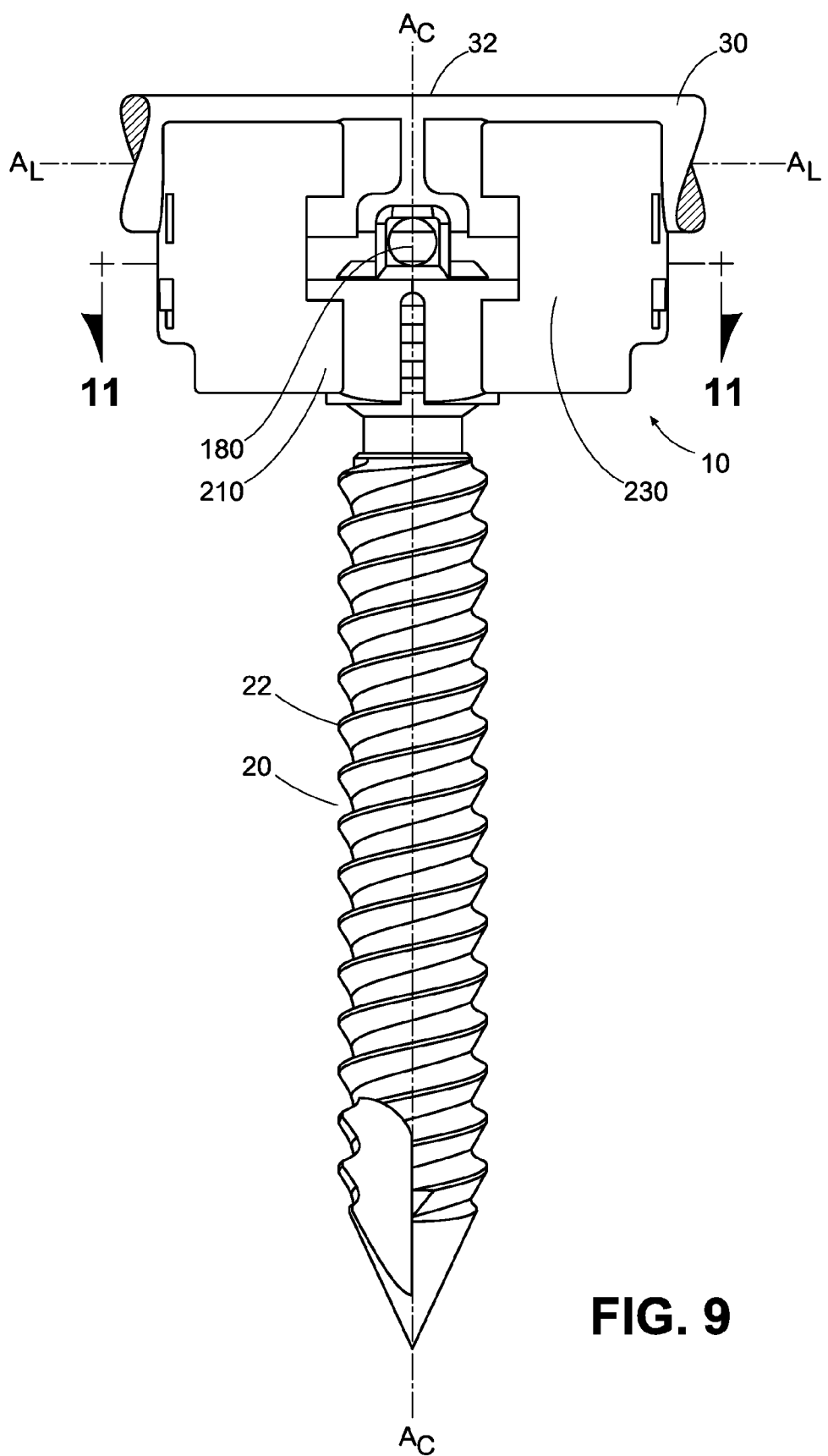
FIG. 9 is a side elevational view of the coupling assembly of FIG. 2 in the open position.
Figure 10:
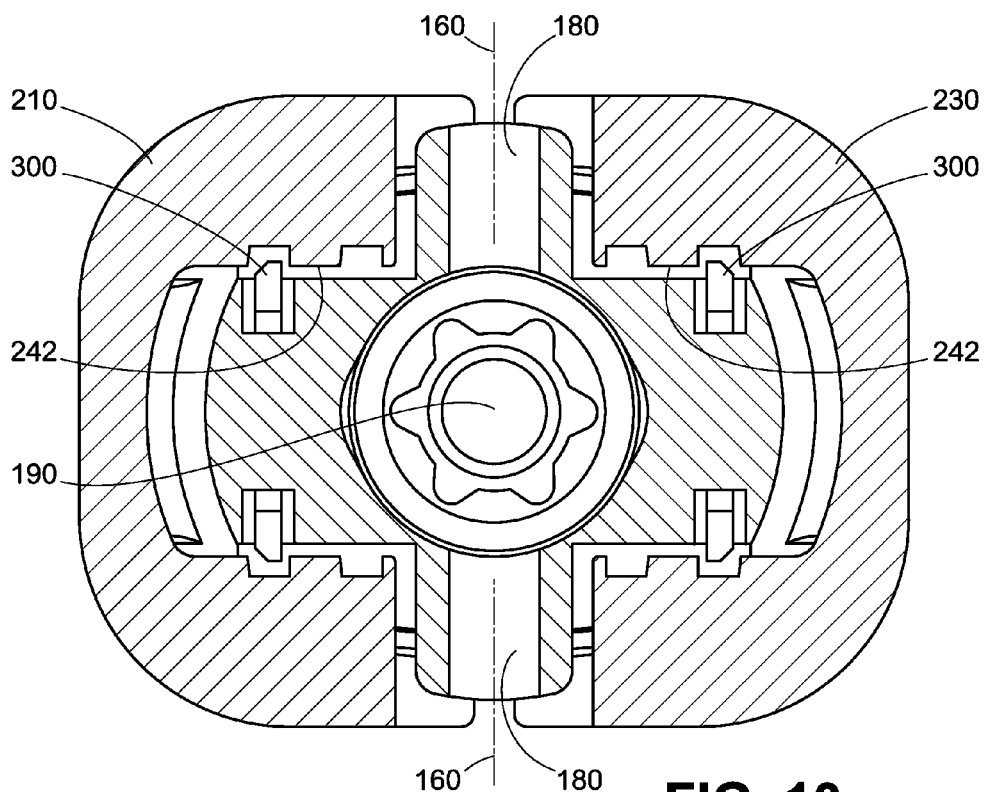
FIG. 10 is a cut-away top plan view of the coupling assembly of FIG. 2 in the closed position, cut along line 10-10 of FIG. 8.
Figure 11:
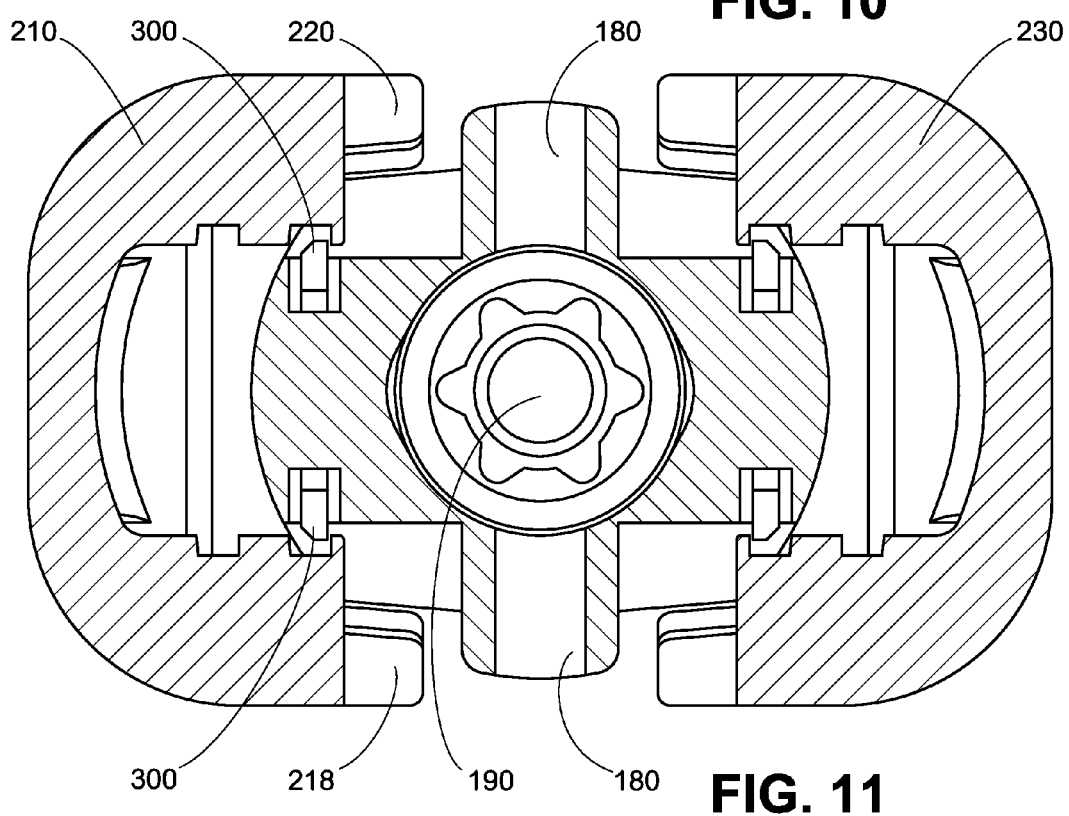
FIG. 11 is a cut-away top plan view of the coupling assembly of FIG. 2 in the open position, cut along line 11-11 of FIG. 9.
Figure 12:
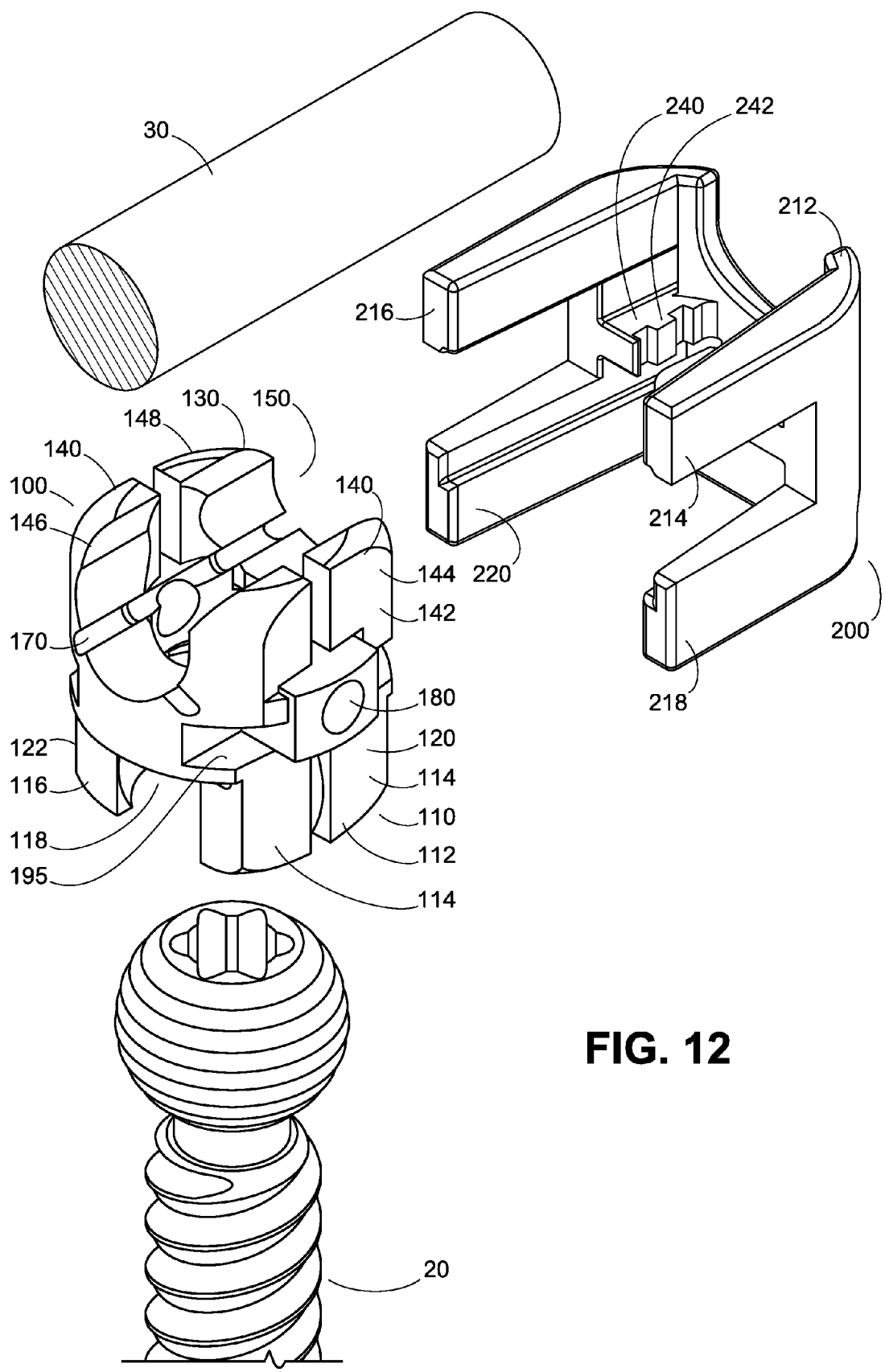
FIG. 12 is an exploded perspective view of one aspect of a coupling assembly having an outer housing with one slider.
Figure 13:
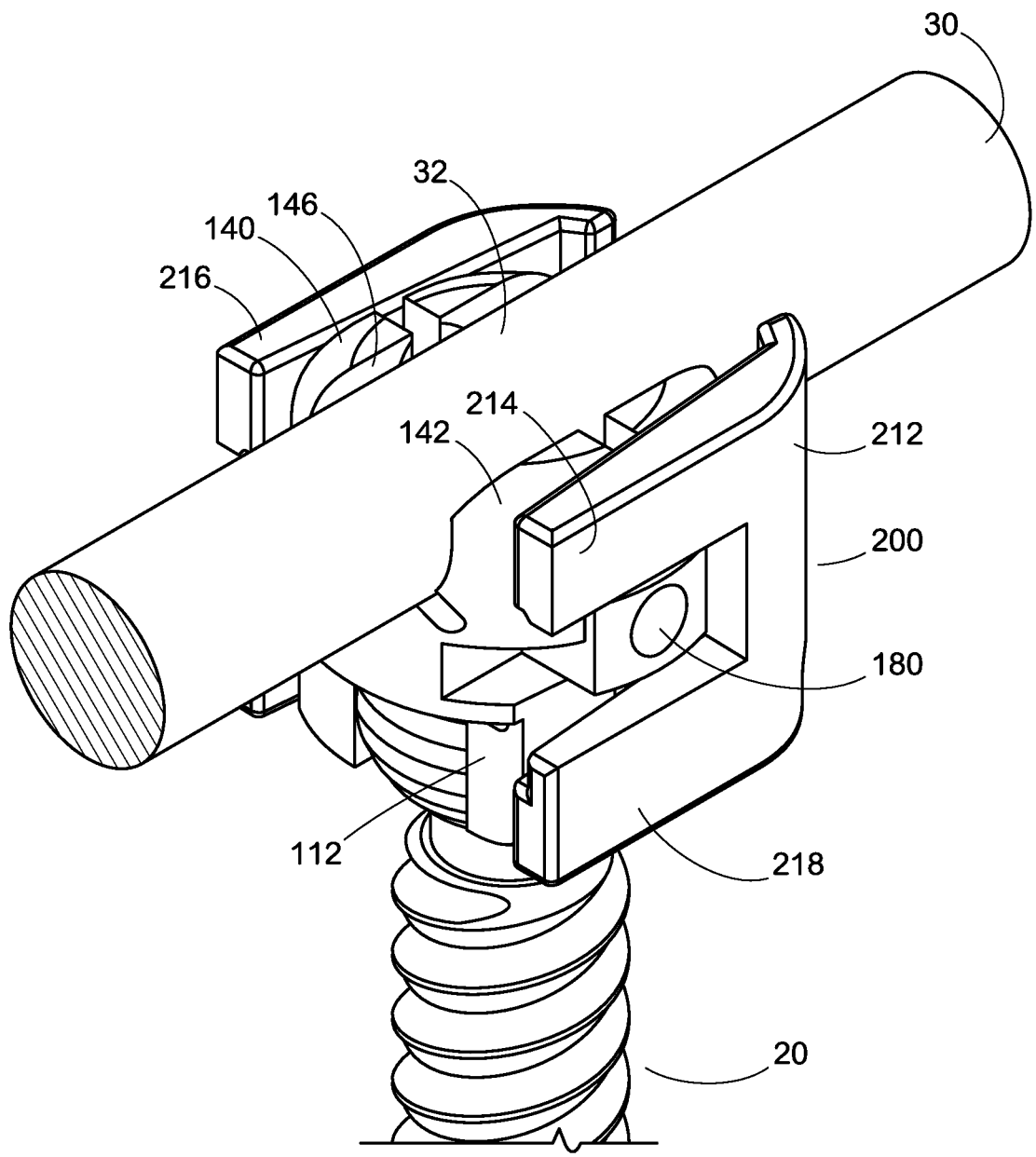
FIG. 13 is a perspective view of the coupling assembly of FIG. 12 in the closed position.

Referring now to FIG. 3, the coupling assembly 10 can further define a tool bore 180 in each side of the saddle configured for receipt of an insertion tool (not shown). Additionally, in one aspect, the coupling element defines an axial driver aperture 190 configured to permit a driver to access a driver bore in the head of the screw.

In another aspect, and referring to FIG. 3, the slider comprises at least one longitudinal beam 240 and the coupling element defines at least one slide channel 195 configured for complimentary receipt of the longitudinal beam 240 to permit the slider to slide longitudinally with respect to the coupling element. In this aspect, a locking feature can also be incorporated. As such, the at least one longitudinal beam defines at least one rib 242 therein and a bias element 300 can be at least partially disposed within the slide channel 195 configured to bias inwardly away from the slide channel. When the bias element biases inwardly, it permits the slider to move longitudinally in the slide channel. When the bias element returns to its original position, back into the slide channel, it engages the at least one rib and substantially fixing the position of the respective slider with respect to the coupling element.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

I claim:

1. A coupling assembly used to selectively couple a bone screw having an elongate shaft and a head to an elongate rod, the coupling assembly comprising:

a coupling element having a top, a bottom, and a central axis extending substantially centrally through the top and bottom, wherein a portion of the coupling element defines a saddle with a first side having an exterior surface and a second side having an exterior surface, the saddle defines a rod receiving channel with a longitudinal axis substantially transverse to the central axis, wherein the bottom of the coupling element defines an aperture through which the elongate shaft of the bone screw is received; and an outer housing having a first slider that is slidable in a direction toward and substantially transverse to the central axis, from a first position where the saddle is substantially open, thereby permitting ingress or egress of the elongate rod with respect to the rod receiving channel, to a second position where at least a portion of the slider frictionally engages an exterior surface of the saddle, biasing the respective side of the saddle toward the longitudinal axis to engage the elongate rod, thereby substantially retaining the elongate rod therein the rod receiving channel.

2. The coupling assembly of claim 1, wherein, when the elongate rod is engaged by the portion of the top of the coupling element, the coupling element does not extend above a top most portion of elongate rod.

3. The coupling assembly of claim 1 wherein the outer housing comprises a first slider comprising a body and first and second spaced legs, the body configured to slide substantially parallel to the longitudinal axis, toward the central axis, from the first position to the second position where at least one of the legs frictionally engages a respective exterior surface, biasing the respective side of the saddle toward the longitudinal axis to engage the elongate rod, thereby substantially retaining the elongate rod therein the rod receiving channel.

4. The coupling assembly of claim 3, wherein the outer housing further comprises a second slider, oppositely disposed from the first slider, wherein the first slider is configured to slide toward a midline portion of the coupling element from a first direction, and wherein the second slider is configured to slide to the midline portion of the coupling element from a second direction.

5. The coupling assembly of claim 3, wherein the coupling assembly does not extend upwardly above a top most portion of the elongate rod.

6. The coupling assembly of claim 3, wherein the saddle is shaped to substantially conform to an exterior portion of the elongate rod.

7. The coupling assembly of claim 3, wherein a portion of the bottom of the coupling element defines a cradle with a first side having an exterior surface and a second side having an exterior surface, the cradle defining a cavity configured for receipt of the head of the bone screw, wherein at least one of the exterior surfaces of the first or second sides of the cradle is angled with respect to the longitudinal axis, and wherein the first slider comprises third and fourth spaced legs, wherein, when the body is in the first position, the cradle is substantially open, thereby permitting movement of the head of the bone screw within the cavity, and when the body is moved into the second position, at least one of the third or fourth legs frictionally engages the angled exterior surface of the respective side of the cradle, biasing the respective side of the cradle toward the longitudinal axis, at least partially closing the cradle, thereby substantially fixing the orientation of the head of the bone screw with respect to the coupling element.

8. The coupling assembly of claim 7, wherein the third and fourth spaced legs are substantially integral with the first and second spaced legs.

9. The coupling assembly of claim 3, wherein both of the exterior surfaces of the first and second sides of the saddle are angled with respect to the longitudinal axis.

10. The coupling assembly of claim 4, wherein the exterior surface of the first side angles away from the longitudinal axis toward the midline, and wherein the exterior surface of the second side angles away from the longitudinal axis toward the midline.

11. The coupling assembly of claim 10, wherein the portion of the at least one leg of the slider that frictionally engages the angled exterior surface is an interior portion, and wherein the interior portion of the at least one leg of the slider is angled to compliment the exterior surface of the respective side in which it frictionally engages.

12. The coupling assembly of claim 3, wherein the coupling element comprises a substantially deformable material.

13. The coupling assembly of claim 12, wherein the substantially deformable material comprises titanium.

14. The coupling assembly of claim 13, wherein at least one of the first and second sides of the saddle defines a longitudinal slot configured to permit the saddle to deform inwardly toward the longitudinal axis.

15. The coupling assembly of claim 12, wherein the slider comprises a material sufficiently hard to deform the coupling element.

16. The coupling assembly of claim 15, wherein the slider comprises cobalt chromium.

17. The coupling assembly of claim 3, wherein each side of the saddle is bisected in the axial direction.

18. The coupling assembly of claim 3, wherein the coupling assembly defines a tool bore in each side of the saddle configured for receipt of an insertion tool.

19. The coupling assembly of claim 3, wherein the coupling element defines an axial driver aperture configured to permit a screw driver to access a driver bore in the head of the screw.

20. The coupling assembly of claim 3, wherein the slider comprises at least one longitudinal beam and the coupling element defines at least one slide channel configured for complimentary receipt of the longitudinal beam to permit slider to slide longitudinally with respect to the coupling element.

21. The coupling assembly of claim 20, wherein the at least on longitudinal beam defines at least one rib therein.

22. The coupling assembly of claim 21, further comprising a bias element at least partially disposed within the slide channel configured to bias inwardly away from the slide channel, thereby permitting the slider to move longitudinally in the slide channel, and bias back into the slide channel, thereby engaging the at least one rib and substantially fixing the position of the slide with respect to the coupling element.

* * * * *